United States Patent
Al-Khattaf et al.

(10) Patent No.: US 9,656,928 B2
(45) Date of Patent: May 23, 2017

(54) PROCESSES AND CATALYSTS FOR PRODUCTION OF LIGHT OLEFINS

(71) Applicant: King Fahd University of Petroleum and Minerals, Dhahran (SA)

(72) Inventors: Sulaiman Saleh Al-Khattaf, Dhahran (SA); Arudra Palani, Dhahran (SA); Abdullah Mohammed Aitani, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 175 days.

(21) Appl. No.: 14/538,993

(22) Filed: Nov. 12, 2014

(65) Prior Publication Data

US 2016/0130197 A1    May 12, 2016

(51) Int. Cl.

| | |
|---|---|
| *C07C 4/00* | (2006.01) |
| *C07C 4/06* | (2006.01) |
| *B01J 29/40* | (2006.01) |
| *B01J 37/06* | (2006.01) |
| *C01B 39/36* | (2006.01) |
| *C01B 39/02* | (2006.01) |

(52) U.S. Cl.
CPC .............. *C07C 4/06* (2013.01); *B01J 29/40* (2013.01); *B01J 37/06* (2013.01); *C01B 39/026* (2013.01); *C01B 39/36* (2013.01); *C07C 2529/035* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 6,713,658 B1 * | 3/2004 | Dath | B01J 29/40 |
| | | | 585/648 |
| 6,951,968 B1 | 10/2005 | Dath et al. | |
| 7,384,883 B2 | 6/2008 | Dath et al. | |
| 2010/0099549 A1 * | 4/2010 | Myers | B01J 38/12 |
| | | | 502/42 |

FOREIGN PATENT DOCUMENTS

| | | | | |
|---|---|---|---|---|
| EP | 109060 A1 | 5/1984 | | |
| GB | 868566 A * | 5/1961 | | C07C 4/06 |
| JP | 04335144 B2 | 9/2009 | | |

OTHER PUBLICATIONS

Sinnott et al., Chemical Engineering Design—Principles, Practice and Economics of Plant and Process Design, 2nd Edition, Elsevier, 2013, pp. 937-940.*

(Continued)

*Primary Examiner* — In Suk Bullock
*Assistant Examiner* — Philip Louie
(74) *Attorney, Agent, or Firm* — Oblon, McClelland, Maier & Neustadt, L.L.P.

(57) ABSTRACT

A novel process and a novel catalyst for the production of light olefins. 1-butene is cracked in the presence of an acid- or base-modified silicalite-1 catalyst bed, wherein the modified silicalite-1 has a Si/Al ratio of greater than 1000. The modification procedures described herein increase the selectivity of the silicalite-1 catalyst toward light olefins such as ethylene and propylene. The catalytic cracking of 1-butene may be carried out in a fixed bed reactor or a fluidized bed reactor.

10 Claims, 2 Drawing Sheets

(56) References Cited

OTHER PUBLICATIONS

Mateo et al., Study on template removal from silicalite-1 giant crystals, Materials Research Bulletin 44, Elsevier, 2009, pp. 1280-1287.*

Palani et al., Silicalite-1 As Efficient Catalyst for Production of Propene from 1-Butene, ACS Publications—Catalysis, Oct. 15, 2014, pp. 4205-4214.*

Jianwen Li, et al. "Catalytic Cracking of Butene to Propylene over Modified HZSM-5 Zeolites," International Journal of Chemical, Nuclear, Metallurgical and Materials Engineering vol. 8 No. 7, 2014. pp. 590-593.

* cited by examiner

PROCESSES AND CATALYSTS FOR PRODUCTION OF LIGHT OLEFINS

BACKGROUND OF THE INVENTION

Technical Field

The present invention relates to processes and catalysts for production of light olefins. More specifically, the present invention relates to modified silicalite-1 catalysts that may be used to convert 1-butene into ethylene and propylene.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Several on-purpose propylene production technologies are being investigated and have some been commercialized, such as methanol-to-olefins (MTO), propane dehydrogenation, catalytic cracking of butenes and olefin metathesis. Among these methods, butene cracking has attracted much attention due to the availability of large and stable supplies of butenes from FCC and stream cracking processes. The process offers refiners and petrochemical producers a high degree of flexibility to their cracking units. Cracking of butenes appears to be a promising technology for production of ethylene and propylene. There is ongoing research on highly reactive yet selective catalysts for the purpose of light olefin production by cracking of butenes. Currently, the catalysts that are being investigated include H-ZSM-5, H-ZSM-48, MCM-22 and PITQ-13. However, most of these catalysts are acidic in nature and favor the production of higher hydrocarbons, especially $C_6+$ aromatics.

Zhu et al. (Applied Catalysis A: General, 2005, v. 288, pp. 134-142—incorporated herein by reference in its entirety) investigated the effects of zeolite pore structure and Si/Al ratio catalytic cracking of 1-butene to propylene and ethylene over medium-pore 10-membered ring zeolites and the small-pore SAPO zeolite. The smaller the pore size of the zeolites, the greater the extent of suppression of the hydrogen transfer reaction of alkenes, and the higher the propylene selectivity.

Lin et al. (Journal of Catalysis, 2014, v. 309, pp. 136-145—incorporated herein by reference in its entirety) reported that the H-ZSM-5 modified with phosphorous to reduce the number of the strong acid sites showed the best performance in catalytic cracking of 1-butene to propylene. It was suggested that adjusting the acid site distribution is important.

Johnson et al. (U.S. Pat. No. 6,222,087—incorporated herein by reference in its entirety) discloses a catalytic cracking process for producing light olefins rich in propylene from $C_4$-$C_7$ olefins using a catalyst containing ZSM-5 and/or ZSM-11 having initial Si/Al ratio greater than about 300 in a fluidized-bed reactor or a fixed-bed swing reactor.

Voskoboynikov et al. (U.S. Pat. No. 7,314,963—incorporated herein by reference in its entirety) discloses a process for producing propylene and ethylene from catalytic cracking of $C_4$-$C_{10}$ olefins over a spherical catalyst comprising MFI-type zeolite having Si/Al ratio between 400 and 500 at 500-600° C.

Dath et al. (U.S. Pat. Nos. 6,951,968 and 7,384,883—each incorporated herein by reference in its entirety) describes a method for producing a catalyst for olefin cracking comprising the steps of heating a ZSM-5 catalyst in steam to remove aluminum from the crystalline silicate framework, extracting aluminum from the pores of the catalyst framework by contacting the catalyst with a complexing agent for aluminum to increase the silicon/aluminum atomic ratio of the catalyst and calcining the catalyst at an elevated temperature.

Colombo et al. (European Patent No. EP0109060A1—incorporated herein by reference in its entirety) discloses a process for the conversion of $C_4$-$C_{12}$ olefins into propylene over zeolites selected from silicalites, boralites, chromosilicates, ZSM-5 and ZSM-11 (Si/Al molar ratio is above 350), at a space velocity of from 5 to 200 kg/h of olefins per kg zeolite and at a temperature of from 400 to 600° C. The silicalite-1 is either ion-exchanged, impregnated, or co-precipitated with a modifying element such as Cr, Mg, Ca, Sr, and Ba.

Heng et al. (Japanese Patent No. JP04335144B2—incorporated herein by reference in its entirety) discloses a process for producing lower olefins (propylene and ethylene) using an MFI zeolite catalyst having Si/Al molar ratio of 280-5000. The variation of $C_4$ olefins in the feed stream (from 0 to 61.2%) was studied and a propylene yield of 32 wt. % was observed at 550° C. using Si/Al molar ratio of 500 and 40 wt. % butenes in a paraffinic feed stream.

In view of the foregoing, the objective of the present invention is to provide new methods and new catalysts for producing ethylene and propylene from butene. The catalysts may be subject to pre-treatment to significantly enhance their production and selectivity toward the light olefins.

BRIEF SUMMARY OF THE INVENTION

According to a first aspect, the present invention relates a process of producing ethylene and propylene comprising contacting 1-butene in a reactor with modified silicalite-1 crystals to catalytically crack the 1-butene to form a mixture comprising ethylene and propylene. The modified silicalite-1 crystals have an MFI framework, a Si/Al ratio of greater than 1000 and are at least one of acid-treated and base-treated.

In one or more embodiments, the catalytic cracking is carried out in the presence of an inert gas.

In one or more embodiments, the catalytic cracking is carried out at a reactor temperature within the range of 450° C. to 750° C.

In one or more embodiments, the catalytic cracking is carried out with an on-stream time of 1 to 5 hours.

In one or more embodiments, the catalytic cracking is carried out at a hydrocarbon partial pressure within the range of 5 psia to 50 psia.

In one or more embodiments, the catalytic cracking is carried out at a gas hourly space velocity of 600 $h^{-1}$ to 10000 $h^{-1}$.

In one or more embodiments, the reactor is selected from the group consisting of a fluidized bed reactor and a fixed bed reactor.

In one or more embodiments, the modified silicalite-1 crystals have an average particle size of 0.02 mm to 1.0 mm in diameter.

In one or more embodiments, the silicalite-1 crystals are calcinated before and/or after acid or base treatment.

In one or more embodiments, the process produces at least 50 wt. % total ethylene and propylene based on the total weight of the 1-butene subject to cracking.

In one or more embodiments, the process produces ethylene and propylene in a ratio (ethylene:propylene) of 1:2 to 1:3.

According to a second aspect, the present invention relates to a process of preparing a silicalite-1 catalyst for catalytic cracking of 1-butene comprising contacting silicalite-1 crystals having an MFI framework and a Si/Al ratio of greater than 1000 with either an acid or a base aqueous solution.

In one or more embodiments, the process further comprises calcination of the silicalite-1 crystals. The acid or base treatment is carried out at a temperature within the range of 80° C. to 120° C.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
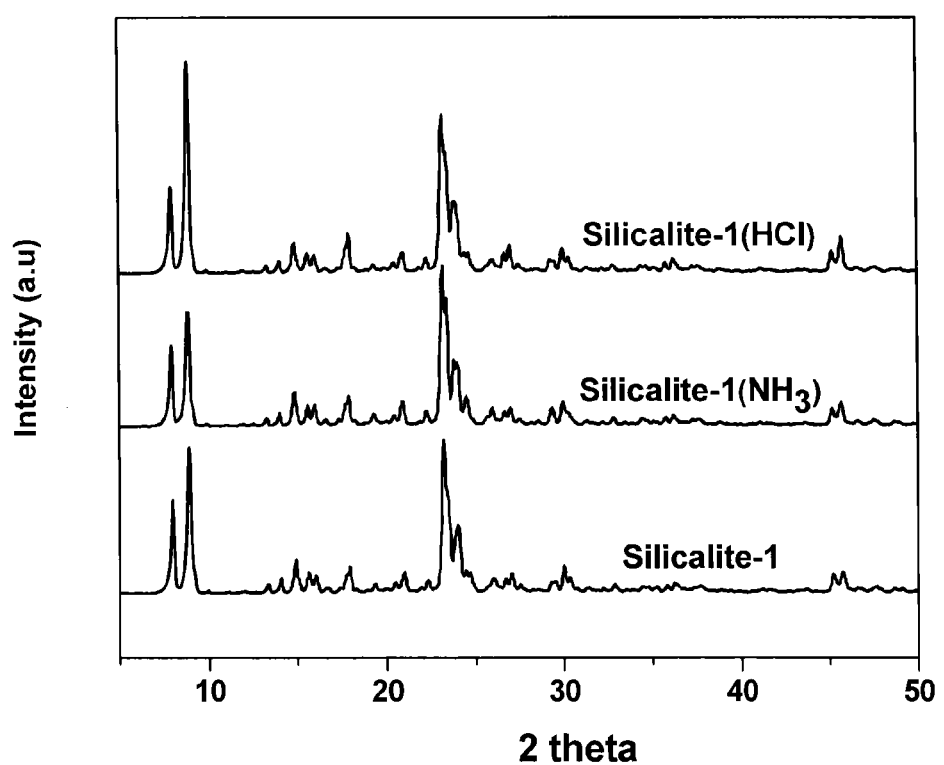
FIG. 1 is a graph illustrating the XRD patterns of silicalite-1, HCl-washed silicalite-1 and $NH_3$-treated silicalite-1.

Referring now to the drawings, wherein like reference numerals designate identical or corresponding parts throughout the several views.

The present invention relates to a process of producing light olefins (i.e. ethylene and propylene) by 1-butene cracking in the presence of modified silicalite-1 catalysts.

Zeolites are crystalline molecular sieves composed mainly of silica and alumina. Silicalite-1 is a type of synthetic zeolite conventionally used to remove harmful organic compounds, such as methyl tert-butyl ether (MTBE) from groundwater. Silicalite-1 has a pentasil MFI framework of intersecting 10 membered-ring pore channels. Silicalite-1 is made without aluminum or, in accordance with the present invention, silicalite-1 is substantially free of aluminum, having a Si/Al ratio of greater than 1000, for example 1000-2500, preferably 1500-2000.

For purposes of the present invention, the Si/Al ratio refers to the Si/Al atomic ratio of the overall crystalline zeolite material and not just the MFI framework, which may be determined by chemical analysis, such as inductively coupled plasma mass spectrometry (ICP-MS).

The silicalite-1 used herein may be synthesized as a powder or an aggregate consisting of small crystals, using a wide variety of techniques, such as a hydrothermal method of growing silicalite-1 crystals. Synthesis processes, aside from catalysts, may further include additives such as binders, structure directing agents or templates (e.g. tetrapropyl ammonium cation). In one embodiment, the silicalite-1 crystals may be of nanorange with an average particle size of no greater than 1000 nm, preferably 50-500 nm, more preferably 50-250 nm. In another embodiment, the silicalite-1 crystals have an average particle size of 0.02-2.5 mm in diameter, preferably 0.1-2.0 mm, more preferably 0.5-1.0 mm. Silica sources for the synthesis of silicalite-1 may be selected from colloidal silica sols or tetraethyl orthosilicate (TEOS) or fumed silica. Examples of colloidal silica sols include Ludox™ (39.8 wt. % $SiO_2$, 0.11 wt. % $Na_2O$, particle size 22-24 nm) and Ludox LS (30.8 wt. % $SiO_2$, 0.108 wt. % $Na_2O$, particle size 11-13 nm).

Other physical properties of the silicalite-1 crystals described herein are $d_{spacing}$ values ranging between 3.5-4.0 (preferably 3.8-3.9), surface area between 350-450 m²/g (preferably 360-430 m²/g), pore volume of 0.15-0.30 cm³/g (preferably 0.18-0.28 cm³/g) and pore diameter of 20-25 Å (preferably 21.5-22.5 Å).

It has been found that treatment of silicalite-1 crystals with either an acid or a base enhances the production of ethylene and propylene from cracking of 1-butene (catalyzed by the modified silicalite-1 crystals). In certain embodiments, cracking of 1-butene in the presence of acid- or base-modified silicalite-1 catalysts produces at least 50 wt. % of ethylene and propylene based on the total weight of 1-butene subject to cracking, preferably 52-52.5 wt. %, more preferably 55-60 wt. %. The amount of ethylene produced is at least 14 wt. %, preferably 14.5-15.5 wt. %, more preferably 16-18 wt. %. Propylene yield, on the other hand, is at least 35 wt. %, preferably 35.5-37.5 wt. %, more preferably 38.5-45 wt. %.

Catalytic cracking of 1-butene in the presence of the acid- or base-modified silicalite-1 catalysts preferably forms a product having an ethylene/propylene (E/P) product ratio (wt.:wt.) of 1:2 to 1:3, preferably 1:2.2 to 1:2.8.

Compared to unmodified silicalite-1 crystals, the improvement in the overall ethylene and propylene yield is at least 20%. In one embodiment, the yield improvement is greater than 30%. In yet another embodiment, the yield improvement is greater than 35%. The E/P product ratio is 1.3 to 1:5.

Cations are typically required to balance the net negative charge on a zeolite framework created by the presence of $AlO_4^{5-}$ anions. These charge-balancing cations are later exchanged into $H^+$ cations, therefore forming Bronsted acid sites (strong acid sites). It is known that four types of OH groups exist on the surface of silicalite-1. These are terminal silanol, geminal silanol, vicinal silanol and nest silanol. The strength of these OH groups was reported to be in the order, terminal<germinal<vicinal<nest. It was reported that pKa of the terminal silanol on silica was 4.9 at room temperature. The OH groups on silicalite-1 are assumed to increase their acid strength as the temperature increases, and act as Brønsted acid at a high temperature. Actually, the nest silanol groups are recognized to be active sites for an acid-catalyzed reaction of Beckmann rearrangement of cyclohexanone oxime to ε-caprolactam carried out in the temperature range 350-400° C. The more plausible as active sites for propene formation was examined by originating strong acid sites from a trace amount of Al in silicalite-1 or the surface silanol groups, by treating silicalite-1 with HCl to dealuminate and with $NH_3$ to enrich the surface silanol groups. It is anticipated that if the strong acid sites act as the active sites, the propene yield would be decreased by HCl treatment, and if the surface silanol groups act as active sites, the propene yield would be increased by $NH_3$ treatment.

By HCl treatment, 15% of Al in silicalite-1 was removed (ICP analysis). The propene yield at 550° C. over the dealuminated silicalite-1 (silicalite-1(HCl)) was increased to a small extent (34.1 to 35.6 C-wt %). By $NH_3$ treatment, the surface OH groups were enriched and the propene yield at 500° C. over the $NH_3$ treated silicalite-1 (silicalite-1($NH_3$)) increased to a considerable extent (34.1 to 39.1 C-wt %). These results are in favor of the possibility that silanol groups are relevant to the formation of propene from 1-butene, though it is not certain which types of silanol groups are relevant to the reaction.

Acids that are suitable for washing of silicalite-1 are preferably strong acids that include, for example, hydrochloric acid, sulfuric acid and nitric acid. Acid solutions may be within a concentration range of 0.1 M to 2 M, preferably 0.5-1.5 M.

In an alternative embodiment, organic acids (with carboxyl group —COOH) such acetic acid, formic acid and citric in the same concentration ranges described above may be used for the washing of silicalite-1.

For base treatment of silicalite-1, preferred bases include NaOH, KOH and ammonia. In one embodiment, silicalite-1 may be treated in an aqueous solution of ammonia and an ammonium salt such as ammonium carbonate, ammonium chloride and ammonium nitrate.

Both the acid and base treatment processes of the silicalite-1 may be carried out for a duration of up 48 h, preferably with heating up to a temperature of 80° C. to 120° C., preferably 90° C. to 110° C.

Furthermore, silicalite-1 crystals prepared according to methods described herein may be subject to a thermal treatment process such as calcination before and/or after the acid/base modification, an elevated temperature such as 600° C. to 800° C., preferably 650° C. to 750° C.

The catalytic cracking of 1-butene may be conducted in a continuous, circulating fluidized-bed reactor or a fixed-bed reactor. A fluidized-bed is simply a fixed-bed through which fluid flows at such a high velocity that the bed is loosened and the particle-fluid mixture behaves as though it is a fluid.

In fluidized catalytic cracking (FCC) processes, a relatively heavy hydrocarbon feedstock admixed with a suitable, immobilized cracking catalyst to provide a fluidized suspension, is cracked in an elongated reactor, or tower, at elevated temperatures to provide a mixture of lighter hydrocarbon products. The reaction products and spent catalysts are discharged from the tower into a separator, e.g. a cyclone unit, located within the upper section of an enclosed stripping vessel, or stripper, with the reaction products being conveyed to a product recovery zone and the spent catalysts entering a dense catalyst bed with the lower section of the stripper.

The hydrocarbon feedstock used for the catalytic cracking process described herein contains at least 95 wt. % 1-butene, preferably more than 98 wt. %, even more preferably more than 99 wt. %. Impurities that may be present in the 1-butene include butadiene, isobutene, 2-butene (cis- and trans-) and isobutylene. Small amounts of higher linear olefins such as pentenes or hexenes may also be present in the feedstock. These small amounts are generally no more than 0.005 wt. %, for example 0.002%-0.003%, preferably 0.001%-0.002%. The 1-butene may be prepared by various methods, including purification by distillation (e.g. fractionation, extractive, etc.) from $C_4$ mixtures from refineries and stream cracking units. In particular, 1-butene may be purified from a feedstock comprising a $C_4$ cut from an FCC unit in a crude oil refinery or a crude oil refinery for producing methyl tert-butyl ether. Such $C_4$ cuts typically contain about 50 wt. % olefins.

The catalytic cracking of 1-butene may be carried out with an on-stream time of 30 min to 8 h, preferably 1-5 h, and in the presence of an inert gas such as nitrogen. As used herein, on-stream time is the actual time that a reactor is operating and producing products. The reaction may be operated at temperatures between 450° C. and about 700° C., preferably 500° C. to 650° C., more preferably 540° C. to 600° C. Operation conditions also include hydrocarbon partial pressures of 5 psia (35 kPa) to 50 psia (345 kPa), preferably 10-40 psia, more preferably 15-30 psia. Additionally, the gas hourly space velocity (GHSV) based on 1-butene feed may be within the range of 600 $h^{-1}$ to 10000 $h^{-1}$, preferably 700 $h^{-1}$ to 1000 $h^{-1}$, more preferably 800 $h^{-1}$ to 900 $h^{-1}$.

The catalytic cracking of 1-butene produces, apart from target products ethylene and propylene, various hydrocarbon groups depending on the expected pathway to form different products. These hydrocarbon groups include 1-butene (reactant), cis- and trans-2-butene (double bond isomerization products), other olefins (betenes, pentenes, and hexenes) and n-butene isomers (skeletal isomerization and cracking products), alkanes (hydrogen transfer products), aromatics (benzene, toluene, xylenes and ethylbenzene; hydrogen transfer products), and $C_8+$ hydrocarbons (aromatics other than benzene, toluene, xylenes and ethylbenzene, alkanes and olefins; oligomerization and hydrogen transfer products). The acid or base-modified silicalite-1 crystals as the cracking catalyst for 1-butene, as previously described, can improve light olefin yields due to minimum side reactions such as isomerization and hydrogen transfer reactions which lead to higher formation of $C_8+$ including higher alkanes and aromatics.

The examples below are intended to further illustrate protocols for preparing, treating and modifying silicalite-1 with an acid or a base and protocols for assessing the catalytic activity of the modified silicalite-1 described herein, and are not intended to limit the scope of the claims.

Example 1

Preparation of Silicalite-1

4.26 g tetrapropylammonium bromide (TPABr) and 0.74 g ammonium fluoride ($NH_4F$) are dissolved into 72 ml of water. Then, 12 g of fumed silica was added and stirred until a homogeneous gel was formed. The gel was subject to hydrothermal crystallization process at 200° C. for 2 days. The molar composition of the gel is 1 $SiO_2$: 0.08 TPABr: 0.10 $NH_4F$: 20 $H_2O$. The gel was washed with water and dried at 80° C. overnight. The template was then removed by calcination at 750° C. for 6 h in air.

Example 2

Acid Washing of Silicalite-1

Silicalite-1 was subject to acid washing (1 M HCl) at 100° C. for 24 h and washed with $H_2O$. The sample was dried at 110° C. and its catalytic activity was tested. 5 g of silica was mixed with 100 g of an aqueous solution of hydrochloric acid. After this mixture was stirred for 24 h at 40 or 100° C. with reflux cooling, the catalyst was filtered, washed with deionized water, and dried for 4 h at 110° C. The XRD pattern and textural properties of HCl-washed silicalite-1 are presented in FIG. 1 and Table 1, respectively.

Example 3

Base Treatment of Silicalite-1

4 g of Silicalite-1 was filled with 20 g of a mixture of aqueous solutions of ammonia (25 wt. %) and ammonium nitrate (7.5 wt. %) into a glass beaker. This was kept into a polypropylene bottle and stirred at 90° C. and autogeneous pressure for 1 h. The sample was then washed with deionized water, filtered, and dried at 110° C. for 4 h. The XRD pattern and textural properties of NH$_3$-treated silicalite-1 are presented in FIG. 1 and Table 1, respectively.

The surface areas of the catalyst sample were measured by nitrogen adsorption at −195° C. with Autosorb-1 (Quanta Chrome), BET equation being applied to the isotherm.

All samples exhibited characteristic peaks of MFI structure in the ranges 2θ=7–10° and 22-25°. Three major peaks were observed for all the samples. The first peak observed at about 2θ=7.9 is superposition of the diffractions from (−1 0 1), (0 1 1) and (1 0 1) faces, diffraction from (0 1 1) face being the main peak. The second peak observed at about 2θ=8.9 is superposition of the diffraction from (0 2 0), (2 0 0), (−1 1 1) and (1 1 1) faces, the diffractions from (0 2 0) and (2 0 0) faces being dominant. The peak observed at about 2θ=23.2 is the diffractions from (5 0 1) face.

TABLE 1

Properties of Silicalite-1, HCl-washed silicalite-1 and NH$_3$-treated silicalite-1.

| Sample/Example | $d_{spacing}$ (Å)[a] | Si/Al molar ratio[b] | Surface Area (m$^2$/g) | $V_{total}$[c] (cm$^3$/g) | Pore diameter (Å) |
|---|---|---|---|---|---|
| Silicalite-1 | 3.825 | 2165 | 425 | 0.28 | 21.8 |
| Acid-washed silicalite-1 | 3.802 | 2499 | 400 | 0.23 | 21.8 |
| Base-treated silicalite-1 | 3.889 | 2035 | 367 | 0.19 | 22.3 |

[a] Evaluated by XRD;
[b] Si/Al molar ratio by ICP analysis;
[c] Total pore volume.

Example 4

Catalytic Activity of Modified Silicalite-1

The catalytic performance of the modified silicalite-1 catalysts was evaluated in a fixed-bed packed with 2 ml of catalyst with a particle size of 0.5-1.0 mm diameter. The catalyst sample was pre-treated in a nitrogen stream at 550° C. for 1 h and then a mixture of the 1-butene and nitrogen (5 ml/min and 25 ml/min, respectively) (GHSV=900 h$^{-1}$) was passed through the catalyst bed at 550° C. The products were analyzed by on-line GC equipped with a GS-Gaspro column and a flame ionization detector (FID).

Figure 2:
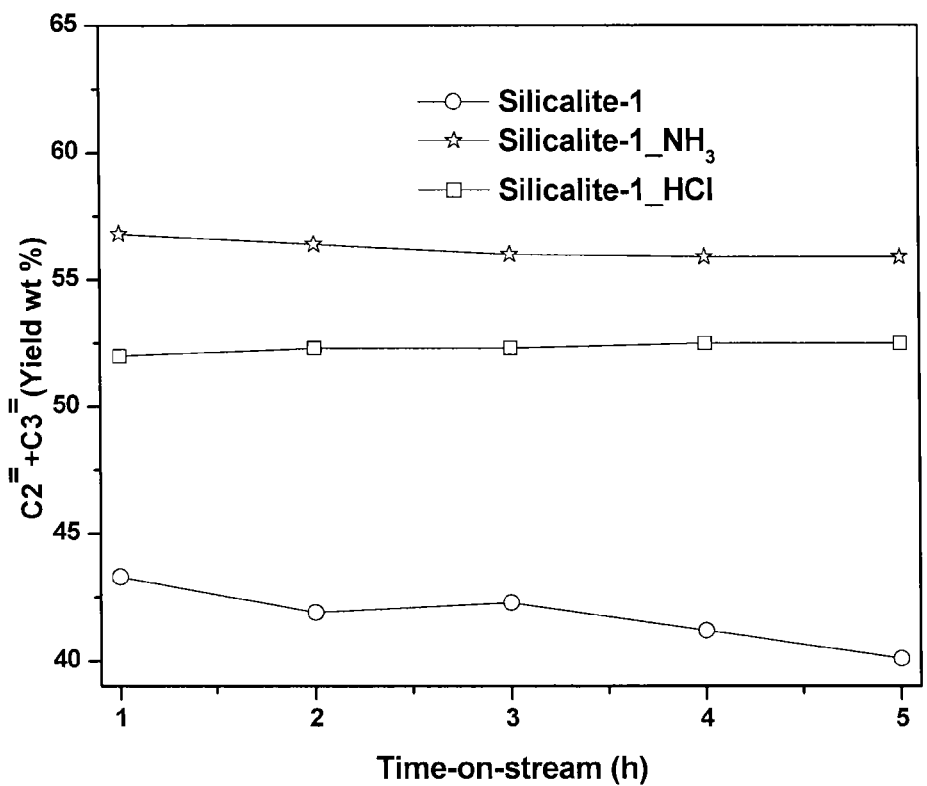
FIG. 2 is a graph illustrating the effect of time on stream on the yields of ethylene and propylene over silicalite-1, HCl-washed silicalite-1 and $NH_3$-treated silicalite-1 from 1-butene cracking at 550° C.

The results of catalytic performance of silicalite-1 and modified silicalite-1 samples for 1-butene cracking are presented in Tables 2 to 4. The changes in the total composition of ethylene and propylene as a function of time on stream are shown in FIG. 2 for silicalite-1 and modified silicalite-1 samples. The activity decay and changes in the light olefins composition were small for the time on stream of 1-5 h.

TABLE 2

Catalytic cracking of 1-butene over silicalite-1 at 550° C.

| | Time-on-Stream (h) | | | | |
|---|---|---|---|---|---|
| Parameter | 1.0 | 2.0 | 3.0 | 4.0 | 5.0 |
| Product yield, wt % | | | | | |
| Methane | 0.0 | 0.0 | 0.0 | 0.0 | 0.0 |
| Ethane | 0.0 | 0.0 | 0.0 | 0.0 | 0.0 |
| Ethylene | 9.3 | 8.3 | 8.1 | 7.6 | 7.2 |
| Propane | 1.4 | 1.0 | 0.9 | 0.9 | 0.8 |
| Propylene | 34.0 | 33.5 | 34.2 | 33.6 | 32.9 |
| Butanes | 3.7 | 3.1 | 3.0 | 2.8 | 2.7 |
| 1-Butene | 6.2 | 7.0 | 7.6 | 7.9 | 8.0 |
| trans-2-Butene | 8.1 | 9.0 | 9.8 | 10.2 | 10.5 |
| Iso-Butylene | 13.5 | 15.2 | 16.5 | 17.1 | 17.6 |
| cis-2-Butene | 6.2 | 7.0 | 7.6 | 7.8 | 8.1 |
| Pentenes | 7.0 | 7.8 | 8.5 | 8.9 | 9.2 |
| Hexenes | 0.7 | 0.7 | 0.8 | 0.8 | 0.8 |
| Benzene | 0.9 | 0.6 | 1.7 | 1.5 | 1.4 |
| Toluene | 3.2 | 2.2 | 1.2 | 1.0 | 0.9 |
| Xylenes + EB | 1.2 | 1.6 | 0.0 | 0.0 | 0.0 |
| C$_8$+ | 4.5 | 3.0 | 0.1 | 0.0 | 0.1 |

TABLE 3

Catalytic cracking of 1-butene over HCl-washed silicalite-1 at 550° C.

| | Time-on-Stream (h) | | | | |
|---|---|---|---|---|---|
| Parameter | 1.0 | 2.0 | 3.0 | 4.0 | 5.0 |
| Product yield, wt. % | | | | | |
| Methane | 1.1 | 1.0 | 1.0 | 1.0 | 1.0 |
| Ethane | 0.6 | 0.6 | 0.5 | 0.5 | 0.5 |
| Ethylene | 16.5 | 16.1 | 15.7 | 15.5 | 15.2 |
| Propane | 3.2 | 2.9 | 2.8 | 2.7 | 2.6 |
| Propylene | 35.6 | 36.2 | 36.6 | 37.0 | 37.3 |
| Butanes | 4.4 | 4.2 | 4.1 | 4.0 | 3.9 |
| 1-Butene | 4.1 | 4.3 | 4.5 | 4.6 | 4.7 |
| trans-2-Butene | 4.8 | 5.1 | 5.3 | 5.4 | 5.5 |
| Iso-Butylene | 8.5 | 8.9 | 9.3 | 9.5 | 9.7 |
| cis-2-Butene | 3.9 | 4.0 | 4.2 | 4.3 | 4.4 |
| Pentenes | 4.1 | 4.2 | 4.4 | 4.5 | 4.6 |
| Benzene | 2.4 | 2.3 | 2.1 | 2.0 | 1.8 |
| Toluene | 7.5 | 7.0 | 6.6 | 6.3 | 6.0 |
| Xylenes + EB | 3.4 | 3.2 | 3.0 | 2.9 | 2.9 |
| C$_8$+ | 0.0 | 0.0 | 0.0 | 0.0 | 0.0 |

TABLE 4

Catalytic cracking of 1-butene over NH$_3$-treated silicalite-1 at 550° C.

| | Time-on-Stream (h) | | | | |
|---|---|---|---|---|---|
| Parameter | 1.0 | 2.0 | 3.0 | 4.0 | 5.0 |
| Product yield, wt. % | | | | | |
| Methane | 0.9 | 0.9 | 0.0 | 0.0 | 0.0 |
| Ethane | 0.5 | 0.5 | 0.0 | 0.0 | 0.0 |
| Ethylene | 17.7 | 16.9 | 15.3 | 14.9 | 14.7 |
| Propane | 3.0 | 2.7 | 3.2 | 2.9 | 2.7 |
| Propylene | 39.1 | 39.5 | 40.7 | 41.0 | 41.2 |
| Butanes | 3.9 | 3.8 | 4.2 | 4.1 | 4.0 |
| 1-Butene | 4.2 | 4.5 | 4.8 | 4.9 | 5.0 |
| trans-2-Butene | 4.9 | 5.2 | 5.8 | 6.0 | 6.1 |
| Iso-Butylene | 8.6 | 9.1 | 9.8 | 10.1 | 10.3 |
| cis-2-Butene | 3.9 | 4.1 | 4.5 | 4.6 | 4.7 |
| Pentenes | 4.2 | 4.3 | 5.4 | 5.5 | 5.6 |
| Benzene | 1.4 | 1.3 | 0.8 | 0.7 | 0.7 |
| Toluene | 5.0 | 4.7 | 3.0 | 2.8 | 2.7 |
| Xylenes + EB | 2.7 | 2.5 | 2.2 | 2.0 | 2.0 |

TABLE 4-continued

Catalytic cracking of 1-butene over
NH$_3$-treated silicalite-1 at 550° C.

| Parameter | Time-on-Stream (h) | | | | |
|---|---|---|---|---|---|
| | 1.0 | 2.0 | 3.0 | 4.0 | 5.0 |
| C$_8$+ | 0.0 | 0.0 | 0.3 | 0.3 | 0.2 |

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A process of producing ethylene and propylene, comprising:
    treating silicalite-1 crystals to at least one of acid washing and base treatment to produce modified silicalite-1 crystals; and
    contacting 1-butene in a reactor with the modified silicalite-1 crystals to catalytically crack the 1-butene to form a mixture comprising ethylene and propylene; wherein the modified silicalite-1 crystals have an average particle size of 0.02 mm to 1.0 mm in diameter, an MFI framework, and a Si/Al ratio of greater than 1000.

2. The process of claim 1, wherein the catalytic cracking is carried out in the presence of an inert gas.

3. The process of claim 1, wherein the catalytic cracking is carried out at a reactor temperature within the range of 450° C. to 750° C.

4. The process of claim 1, wherein the catalytic cracking is carried out with an on-stream time of 1 to 5 hours.

5. The process of claim 1, wherein the catalytic cracking is carried out at a hydrocarbon partial pressure within the range of 5 psia to 50 psia.

6. The process of claim 1, wherein the catalytic cracking is carried out at a gas hourly space velocity of 600 h$^{-1}$ to 10000 h$^{-1}$.

7. The process of claim 1, wherein the reactor is selected from the group consisting of a fluidized bed reactor and a fixed bed reactor.

8. The process of claim 1, wherein the silicalite-1 crystals are calcinated before and/or after acid washing or base treatment.

9. The process of claim 1, wherein the process produces at least 50 wt. % total ethylene and propylene based on the total weight of the 1-butene.

10. The process of claim 1, wherein the process produces ethylene and propylene in a ratio of ethylene to propylene of 1:2 to 1:3.

* * * * *